(12) United States Patent
Kurfürst et al.

(10) Patent No.: US 8,283,147 B2
(45) Date of Patent: Oct. 9, 2012

(54) PANCREATIN AND METHOD FOR REDUCING THE VIRAL AND MICROBIAL CONTAMINATION OF PANCREATIN

(75) Inventors: Manfred Kurfürst, Moorrege (DE); Christian Rämsch, Groß Nordende (DE); Thomas Schräder, Uetersen (DE); Thomas Moest, Moorrege (DE)

(73) Assignee: Nordmark Arzneimittel GmbH & Co. KG (DE)

( * ) Notice: Subject to any disclaimer, the term of this patent is extended or adjusted under 35 U.S.C. 154(b) by 546 days.

(21) Appl. No.: 12/403,697

(22) Filed: Mar. 13, 2009

(65) Prior Publication Data

US 2009/0233344 A1   Sep. 17, 2009

(30) Foreign Application Priority Data

Mar. 11, 2008 (EP) .................................... 08019210

(51) Int. Cl.
*C12N 9/94* (2006.01)
(52) U.S. Cl. ...................................... 435/186; 435/68.1
(58) Field of Classification Search ........................ None
See application file for complete search history.

(56) References Cited

U.S. PATENT DOCUMENTS

| 3,844,891 A | 10/1974 | Hess et al. |
| 3,956,483 A | 5/1976 | Lewis |
| 2007/0148151 A1 | 6/2007 | Frink et al. |

FOREIGN PATENT DOCUMENTS

| CA | 394981 A | 3/1941 |
| DE | 2106706 A1 | 8/1972 |
| DE | 3248588 A1 | 7/1984 |
| EP | 0583726 A | 2/1994 |
| WO | 2007/014896 A | 2/2007 |

*Primary Examiner* — Hope Robinson
(74) *Attorney, Agent, or Firm* — McCormick, Paulding & Huber LLP

(57) ABSTRACT

The invention relates to a method for producing pancreatin with reduced viral and microbial contamination, comprising the steps of (a) providing the pancreatin in solid form with a residual moisture of 0.5 weight % or less, down to almost zero, based on the pancreatin provided; (b) subjecting the pancreatin provided in step (a) to a heat treatment at a temperature of 84° C., preferably 80° C. and below; wherein, the biological activity of the pancreatin obtained in step (b) corresponds to at least 50% of the biological activity of the pancreatin provided in step (a); and the viral infectiousness of the pancreatin obtained in step (b) has been reduced by a factor of more than 1 $\log_{10}$ in comparison with the viral infectiousness of the pancreatin provided in step (a), as well as a pancreatin produced according to this method and its use for producing a medicine or a nutritional supplement.

50 Claims, 3 Drawing Sheets

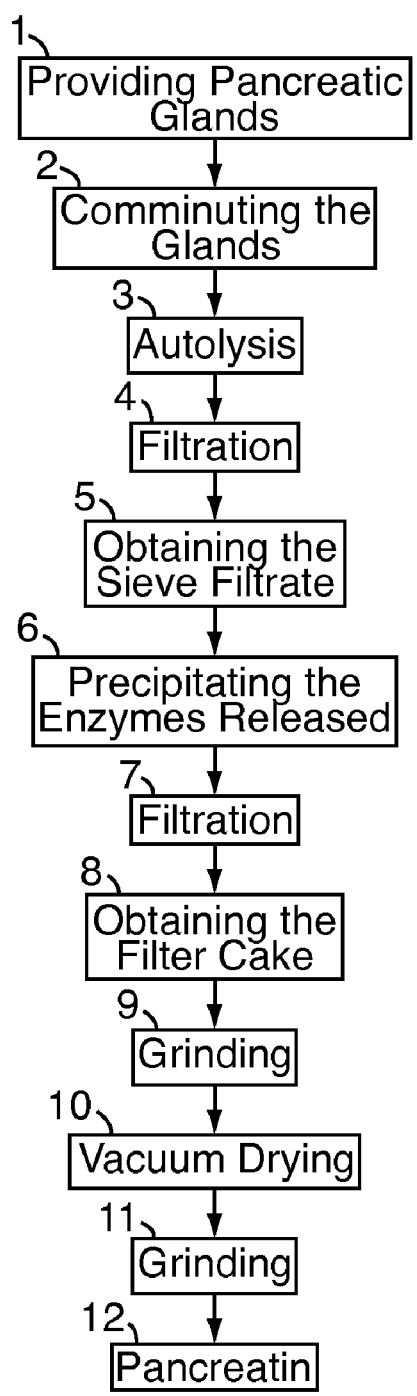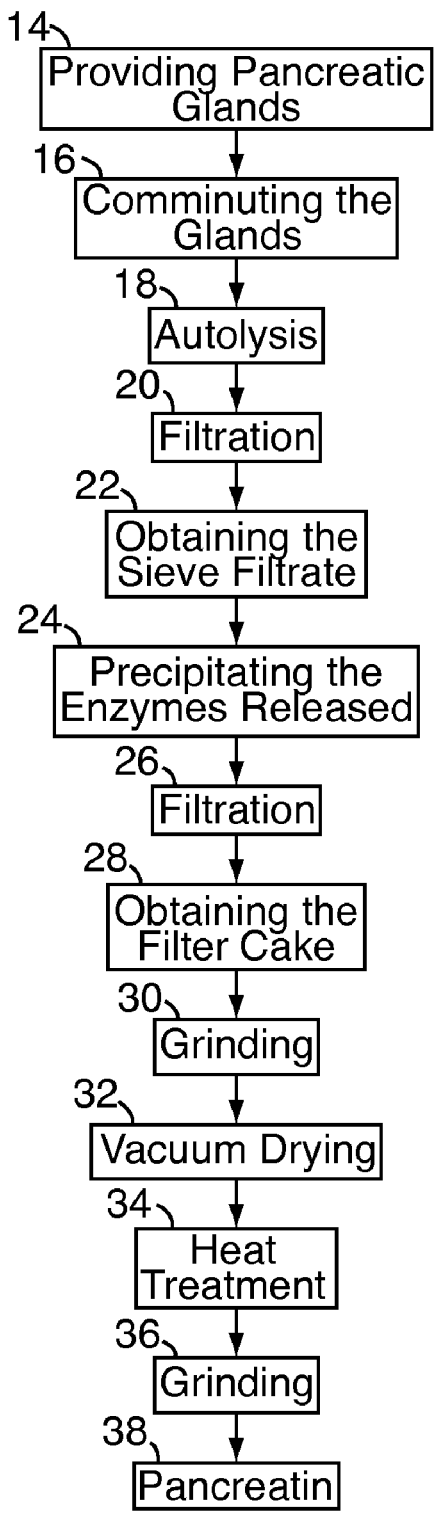

1

PANCREATIN AND METHOD FOR REDUCING THE VIRAL AND MICROBIAL CONTAMINATION OF PANCREATIN

Applicants claim priority benefit under 35 U.S.C. 119(e) under a prior-filed foreign application—European No. 08019210.7 filed Mar. 11, 2008.

FIELD OF THE INVENTION

The invention relates to pancreatin and a method for reducing the viral and microbial contamination of pancreatin, pancreatin produced using this method and also uses of such pancreatin.

BACKGROUND OF THE INVENTION

Pancreatin is obtained as an extract from animal pancreatic glands. Extracts of this type, which are obtained from biological raw material, can exhibit a high degree of viral contamination. Viruses are nucleic acids which are surrounded by a protein coat. Enveloped viruses also have an outer lipid envelope in addition. As viruses cannot replicate independently, they are dependent on hosts. Consequently, they are present in practically all living organisms on Earth. Very few of the known viruses are pathogenic for humans, as they have a high degree of host specificity. In order to rule out endangerment of the consumer from the beginning, extracts that are intended for human consumption or that are used as active agent in medicines should fundamentally have a viral contamination which is as low as possible or no viral contamination. It is not always the case that the actual production method leads to a significant inactivation or removal of the viruses present, so that, particularly when producing pharmaceutical active agents, additional reduction or inactivation steps must be integrated into the method.

Many methods are described for the reduction or inactivation of viruses and microorganisms [K. H. Wallhäuser, Praxis der Sterilisation Desinfektion Konservierung [Practice of Sterilization, Disinfection and Preservation], Thieme Verlag, Stuttgart 1995]. In addition to mechanical removal by e.g. chromatography or filtration, these contaminations can be inactivated selectively by the addition of chemical compounds. The latter method is however problematic insofar as these compounds must be completely removed again so that they do not cause any toxic effects in the end product. Physical methods such as e.g. heat treatment or irradiation are likewise well-established methods for inactivating viruses or microorganisms.

A particular challenge is the inactivation or removal of viruses from complex biological extracts whose active substance is enzyme mixtures, without destroying or changing the enzymatic activity of the proteins in the process.

Of particular economic interest is the pharmaceutical active agent pancreatin which is obtained as an extract from porcine pancreas and is used in dried form as an oral therapeutic agent, as described in German Patent DE 3248588 A1.

A known method for producing pancreatin is described hereinafter with reference to FIG. 1. The pancreatic glands 1 which came from domestic pigs are first comminuted 2 and subjected to autolysis 3. By filtering 4 the intermediate product obtained in this manner, the sieve filtrate is obtained 5. The enzymes which are present in the sieve filtrate are then precipitated 6, the mixture is filtered 7 and the filter cake is obtained 8. The filter cake obtained is finally ground 9, vacuum dried 10 and ground once more, whereby the pancreatin is obtained. The method steps designated with the reference numbers 2 to 10 in each case lead to intermediate products which are designated in the following as intermediate stages.

The active substances in pancreatin are various polymer-degrading enzymes such as lipases, amylases and proteases, amongst others. A prerequisite for the effectiveness of the therapy is that all enzymes are present in the active agent in a certain ratio and in active form.

Investigations into the viral contamination of pancreatin have shown that porcine parvovirus (PPV) is detectable as a single virus in pancreatin as an infectious particle. The zoonotic viruses EMCV, PEV9 and HEV and as well as rotavirus and reovirus could neither be detected as infectious particles nor at the genomic level. Fundamentally, pharmaceutical active agents should not contain any infectious viruses. Although, according to present knowledge, PPV is not pathogenic for humans, the goal should therefore be a PPV-free pancreatin. PPV is an oft used model virus as it stands out on account of a very high resistance to a wide range of inactivation methods. As the production process described in FIG. 1 is not in the position to completely remove the PPV contamination present, additional virus reduction steps must be implemented.

Classic virus inactivation methods, such as for example dry or wet heat, or virus reduction methods, such as for example filtration or chromatography, cannot be used in most cases for extracts from biological raw material and in particular for organ extracts without changing the composition and/or high product losses.

A method for producing a pancreatin-containing composition in dry powder form is known from U.S. Pat. No. 3,956,483, in which method chopped pancreas is mixed with an aqueous solution which contains calcium sulphate. An enzyme activator is then added to this mixture. After a predetermined period of time for the enzyme activation, the mixture is finally dehydrated, whereby pathogenic bacteria should be inactivated. This inactivation is carried out at temperatures above 160° F. (73° C.), preferably at 180° F. (82° C.). In all of the examples, an inactivation temperature of 82° C. is used.

U.S. Patent Application 2007/0148151 A1 discloses a method for producing pancreatin. To reduce the viral and bacterial contamination this method provides a heating of pancreatin in disperse form, to achieve this, the pancreatin should contain less than 9 weight % of one or a plurality of solvents. The examples show methods in which the proportion of the solvent was at least 1 weight %. The disperse pancreatin is then heated to a temperature of at least 85° C. for a period of time of less than 48 h.

Treatment at 85° C. or even higher temperatures is required according to US 2007/0148151 A1 in order to be able to fulfil the official regulations for virus contamination of biological products. At a temperature of 80° C., the regulations could not be fulfilled.

It is further stated in US Patent Application 2007/0148151 that a heat treatment at 60° C. for 70 hours can damage pancreatin. A heat treatment can destroy a substantial amount of the enzymatic activity of the pancreatin.

It is further known from the prior art that the results of a virus reduction by means of the action of heat depend to a considerable extent on the residual moisture of the samples. The dryer the material which is subjected to the heating, the higher is the resistance of the viruses to high temperatures. From this it follows that the temperature of the heating can be chosen to be lower, the higher is the residual moisture of the material.

SUMMARY OF THE INVENTION

It is an object of the invention to overcome the disadvantages of the prior art. A method for producing pancreatin with reduced viral and microbial contamination shall be presented, which method requires a temperature which is as low as possible and nonetheless brings about a substantial reduction in the viral and microbial contamination. Pancreatin produced using the method and uses of this pancreatin shall further be presented.

Accordingly, the invention includes a pancreatin which is produced by
- (a) Providing the pancreatin in solid form with a residual moisture of 0.5 weight % or less, down to almost zero, based on the pancreatin provided;
- (b) Subjecting the pancreatin provided in step (a) to a heat treatment at a temperature of 84° C., preferably 80° C. and below;

wherein, the biological activity of the pancreatin obtained in step (b) corresponds to at least 50% of the biological activity of the pancreatin provided in step (a); and the viral infectiousness of the pancreatin obtained in step (b) has been reduced by a factor of more than 1 $\log_{10}$ in comparison with the viral infectiousness of the pancreatin provided in step (a).

The pancreatin is further characterized in that the biological activity of the heat-treated pancreatin corresponds to at least 50% of the biological activity of the untreated pancreatin; the viral infectiousness of the heat-treated pancreatin has been reduced by a factor of more than 1 $\log_{10}$ in comparison with the viral infectiousness of the untreated pancreatin; and the germ contamination of the heat-treated pancreatin is smaller than 500 KBE/g.

The residual moisture of the pancreatin provided in step (a) is 0.1 to 0.3 weight %. The heat treatment in step (b) is preferably carried out at 80° C.

The pancreatin provided in step (a) has a residual moisture of 0.3 weight %, wherein the treatment in step (b) is carried out at a temperature of 80° C. and below. The residual moisture can also be lower than 0.3 weight %.

The biological activity of the pancreatin obtained in step (b) corresponds to at least 90% of the biological activity of the pancreatin provided in step (a). The contamination with toxic substances of the pancreatin obtained in step (b) is not higher than the contamination of the pancreatin provided in step (a). The germ contamination of the pancreatin obtained in step (b) is preferably smaller than 500 KBE/g.

The pancreatin in step (b) is subjected to the heat treatment for a time period of 48 hours or less, preferably for 12 to 32 hours. The untreated pancreatin is in this case obtained from porcine pancreas.

According to another aspect of the present invention, a method for producing a pancreatin with reduced viral and microbial contamination, includes the steps of:
- (a) Providing the pancreatin in solid form with a residual moisture of 0.5 weight % or less, down to almost zero, based on the pancreatin provided; and
- (b) Subjecting the pancreatin provided in step (a) to a heat treatment at a temperature of 84° C., preferably 80° C. and below, wherein, the biological activity of the pancreatin obtained in step (b) corresponds to at least 50% of the biological activity of the pancreatin provided in step (a); and the viral infectiousness of the pancreatin obtained in step (b) has been reduced by a factor of more than 1 $\log_{10}$ in comparison with the viral infectiousness of the pancreatin provided in step (a).

According to a production process provided by the present invention, a pancreatin is obtained in the case of which the biological activity of the heat-treated pancreatin corresponds to at least 50% of the biological activity of the untreated pancreatin, the viral infectiousness of the heat-treated pancreatin has been reduced by a factor of more than 1 $\log_{10}$ in comparison with the viral infectiousness of the untreated pancreatin and the germ contamination of the heat-treated pancreatin is smaller than 500 KBE/g.

The use of this pancreatin to produce a medicine or as a nutritional or food product or as a nutritional supplement is further provided.

BRIEF DESCRIPTION OF THE DRAWINGS

FIG. 1 is a simplified illustration that shows a flowchart of a method for producing pancreatin from porcine pancreatic glands according to the prior art;

FIG. 2 is a simplified illustration that shows a flowchart of a method according to the present invention for producing pancreatin from porcine pancreatic glands;

DETAILED DESCRIPTION OF THE PREFERRED EMBODIMENTS

Figure 3:
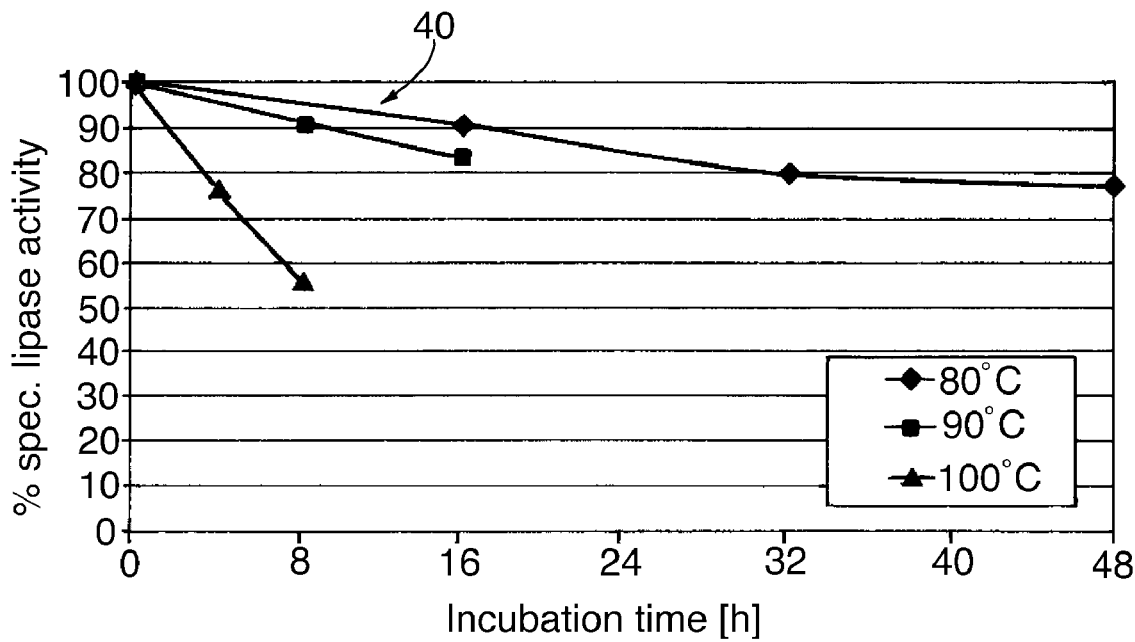
FIG. 3 is a simplified illustration that shows a graph which shows the lipase activity of treated pancreatin samples after different treatment times.

According to the invention, the heat treatment of solid pancreatin which has a residual moisture of 0.5 weight % or less, down to almost zero, is provided. In contrast with the assumptions which were encountered in the prior art, it was found that even at such a low residual moisture an effective reduction of the viral and microbial contamination can be achieved.

Moreover, it was determined that the treatment of pancreatin with the residual moisture specified can take place at a temperature which is 84° C., preferably 80° C. or below. A lower treatment temperature is, in addition to the economic advantage, particularly connected with a better conservation of the original enzymatic activity of the pancreatin enzymes. The reduction of the residual moisture provided according to the invention allowed the drop in enzyme activity (<20%) to be reduced considerably in comparison with the prior art.

The residual moisture of the pancreatin provided in step (a) is, according to the invention, 0.5 weight % or less, preferably 0.1 to 0.3 weight %. Here, the term "residual moisture" is understood to mean the pancreatin's content of one or more solvents, for example water, acetone, isopropanol or mixtures thereof, or other liquids.

One embodiment of the method according to the invention for producing pancreatin with reduced viral and bacterial contamination is described hereinafter with reference to FIG. 2. The pancreatic glands 14 which came from domestic pigs were first comminuted 16 and subjected to autolysis 18. By filtering 20 the intermediate product obtained in this manner, the sieve filtrate is obtained 22. Then, the enzymes which are present in the sieve filtrate are precipitated 24, the mixture is filtered 26 and the filter cake is obtained 28. The filter cake is finally ground 30 and vacuum dried 32 until it has a residual moisture which is 0.1 to 0.3 weight %. Then, the filter cake is subjected to a heat treatment at 80° C. or below 13. The heat-treated filter cake is then ground once more, whereby the prepared pancreatin is obtained 34.

The filter cake obtained in accordance with the previous method (reference number 28 in FIG. 2) still contains a part of the solvent which was used to autolyse the comminuted pancreatic glands (reference number 18 in FIG. 2). This solvent is generally aqueous isopropanol. In spite of the filtration, the filter cake obtained still, due to the method, contains a part of the solvent, which part is further reduced by the vacuum drying and, in the process adjusted to a proportion of 0.1 to 0.3 weight % based on the pancreatin obtained by means of the vacuum drying.

In the present invention, the term "pancreatin" comprises the filter cake designated here with the reference number 8, which is raw pancreatin which is subjected to further treatment steps (reference numbers 30 to 36 in FIG. 2) according to the invention. This filter cake is also termed "untreated pancreatin". The term "pancreatin" further also comprises the pancreatin that has been subjected to the method step (b), i.e. the heat treatment. This pancreatin is also termed "treated pancreatin" here.

The expression "in solid form" means pancreatin which is not present as a solution, emulsion or suspension. For example, the pancreatin can be present in solid ground form, for example as powder or granules.

The heat treatment is typically carried out in an oven. The heat treatment is preferably carried out at a temperature of 70 to 80° C., particularly preferably at 80° C. The temperature should lie below 84° C. The heat treatment should take place using "dry heat".

In a preferred embodiment, the pancreatin provided in step (a) has a residual moisture of 0.3 weight %, wherein this pancreatin is subjected to a heat treatment at 80° C.

The heat treatment is preferably carried out for a period of time of 48 h or less. Preferably the heat treatment is carried out for 1 h to 48 h, more preferably 8 h to 48 h, even more preferably 24 h to 48 h and in particular 24, 32 or 48 h.

The biological activity of the pancreatin obtained in step (b) should correspond to at least 80%, preferably at least 90%, of the biological activity of the pancreatin provided in step (a). With respect to the enzymes which are contained in the pancreatin, the term "biological activity" corresponds to the term "enzymatic activity".

The contamination with toxic substances of the pancreatin obtained in step (b) should further not be higher than the contamination of the pancreatin provided in step (a). The germ contamination of the pancreatin obtained in step (b) should be smaller than 500 KBE/g, preferably not more than 100 KBE/g.

A preferred source from which the untreated pancreatin can be obtained is porcine pancreas.

A method according to the invention can be applied to all virus forms, particularly DNA and RNA viruses, enveloped and unenveloped viruses, furthermore to virions and prions or other similar biological systems and also bacteria and fungi. The method is preferably used to reduce the PPV contamination and/or the reovirus contamination of pancreatin from the porcine pancreas. Additionally or alternatively, the method can be used to reduce the contamination with the following viruses: pseudorabies virus (PRV), bovine viral diarrhoea virus (BVDV), encephalomyocarditis virus (EMCV).

A method according to the invention allows the reduction of the virus and microorganism contamination of pancreatin without its enzymatic activity being substantially reduced, the pharmacologically intended properties being impaired or toxic chemical compounds being produced.

The viral infectiousness of the heat-treated pancreatin should have been reduced by a factor of more than 1 $\log_{10}$, preferably more than 3 $\log_{10}$, particularly preferably more than 4 $\log_{10}$ in comparison with the viral infectiousness before the heat treatment. This is also particularly valid for the viral infectiousness of porcine parvovirus (PPV) and/or the viral infectiousness of reovirus. For example, the PPV infectiousness in pancreatin after the treatment should be reduced by a factor of more than 1 $\log_{10}$, preferably more than 3 $\log_{10}$, particularly preferably more than 4 $\log_{10}$ in comparison with its infectiousness before the treatment.

The viral infectiousness is calculated by endpoint titration and subsequent calculation of the half tissue culture infectious dose ($TCID_{50}$) in accordance with the Spearman-Kärber formula (Bundesanzeiger, No 84, 4 May 1994). The virus titres calculated in this manner are given as $\log_{10} TCID_{50}$ per ml with confidence intervals of 95%.

The reduction in the viral contamination is given in accordance with the EU note for guidance CMMP/BWP/268/95, Annex II, as a logarithmic reduction factor which is the difference in virus titre between a control sample and the heat-treated samples.

The residual moisture is determined using known methods.

The invention is explained hereinafter on the basis of an example. The example shall in no way restrict the scope of the invention.

EXAMPLES

Numerous experiments were carried out in order to investigate the influence of the residual moisture and the temperature at which the heat treatment is carried out on the biological activity and the virus titre of solid pancreatin. The influence of the treatment temperature on the pancreatin stability was investigated first. The specific lipase activity was determined as a measure for the pancreatin stability.

FIG. 3 shows the results of these investigations. The samples investigated had a residual moisture of less than 3.0 weight %, specifically 1.7 weight % before the heat treatment. These samples were heat treated at temperatures of 80, 90 and 100° C. and the lipase activity determined after 8, 16 and 48 h. It can be seen from curves 40 in FIG. 3 that the lipase activity decreases all the more markedly and all the faster, the higher is the treatment temperature.

Figure 4:
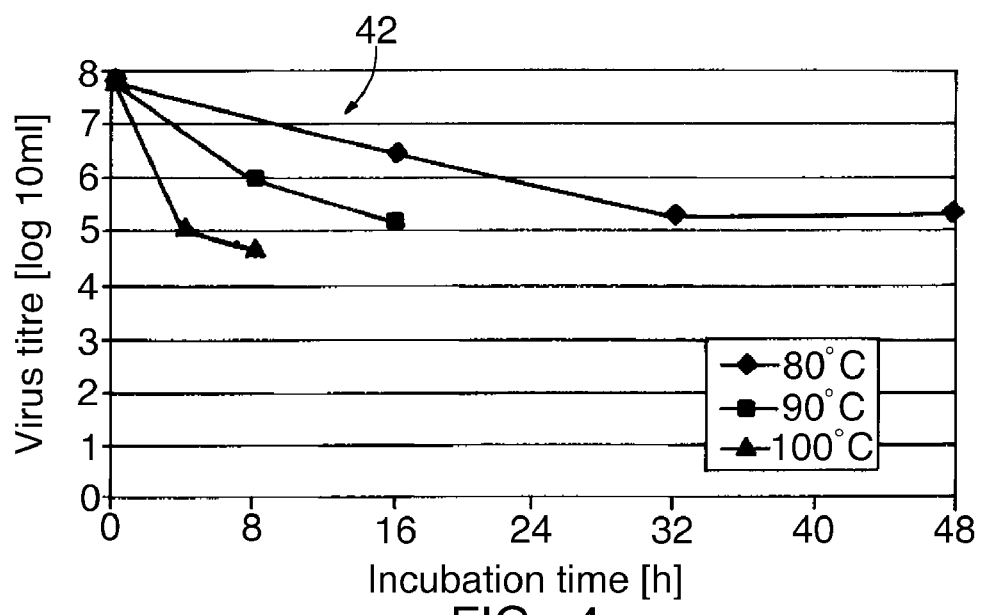
FIG. 4 is a simplified illustration that shows a graph which shows the virus titre of treated pancreatin samples after different treatment times.

FIG. 4 shows the influence of the chosen treatment temperature on the virus titre. As can be seen from curves 42, given a satisfactory treatment time a sufficient decrease in the virus titre is even achieved at a treatment temperature of 80° C.

In further experiments which were carried out, it was determined that an inactivation of viruses, particularly of PPV and reoviruses is even achieved at 80° C. and a very low residual moisture of 0.5 weight % or less, before the heat treatment.

Figure 5:
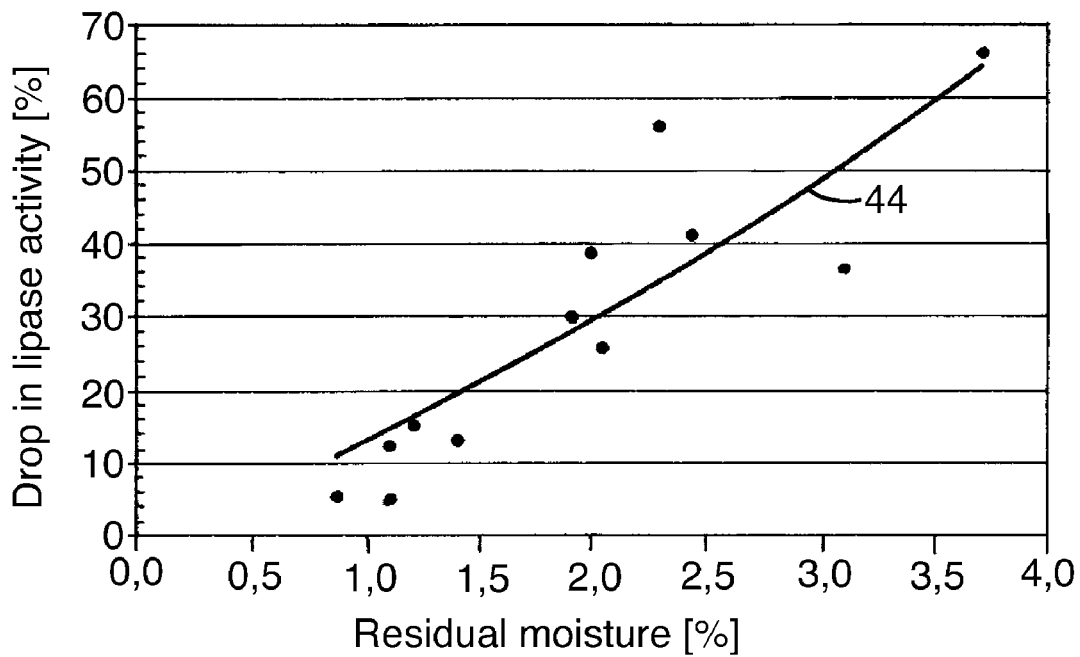
FIG. 5 is a simplified illustration that shows a graph which shows the drop in lipase activity at different residual moistures of the treated pancreatin samples.

FIG. 5 shows a graph in which curve 44 shows the drop in lipase activity of pancreatin following a heat treatment of 24 h at 80° C. It can be seen that at higher residual moistures, the heat treatment is associated with a bigger drop in activity. For this reason, the inventors have decided to investigate the heat treatment of pancreatin which only contains a residual moisture of 0.5 weight % or lower.

Figure 6:
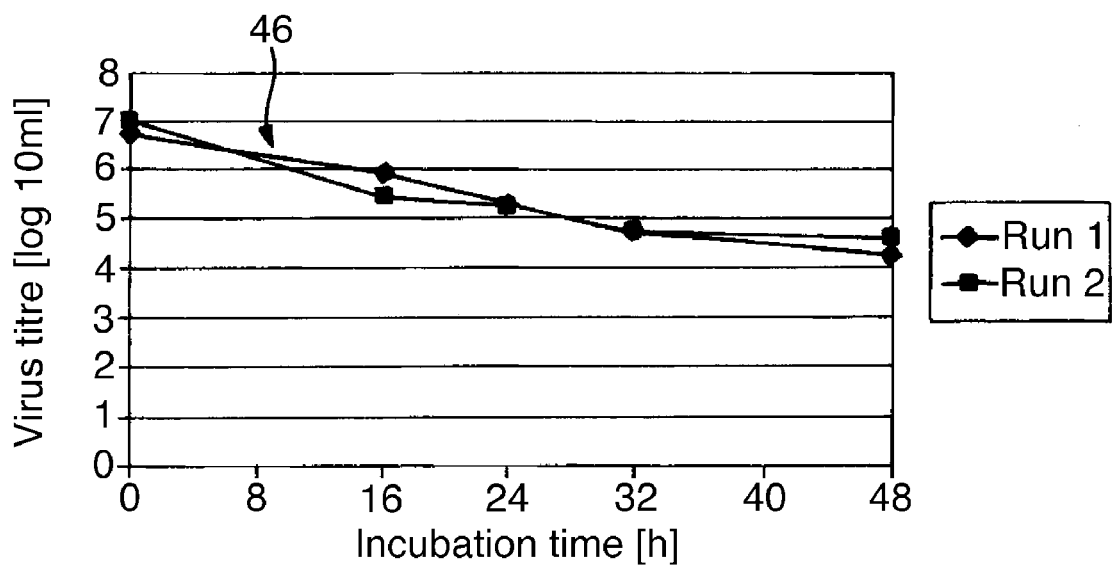
FIG. 6 is a simplified illustration that shows a graph which shows the virus titre of treated pancreatin samples after different treatment times.

The results of the investigation of pancreatin samples which were spiked with PPV are shown in FIG. 6 at curves 46. The residual moisture of these samples was 0.1 to 0.3 weight %. The influence on PPV of the heat treatment at 80° C. is shown for two series of experiments in Table 1:

TABLE 1

| Time [h] | Series No 1[1]<br>Reduction Factors<br>[log₁₀] ± Standard Deviation | Series No 2[2]<br>Reduction Factors<br>[log₁₀] ± Standard Deviation |
|---|---|---|
| 16 | 1.55 ± 0.41 | 0.88 ± 0.55 |
| 24 | 1.81 ± 0.40 | 1.49 ± 0.47 |
| 32 | 2.28 ± 0.38 | 2.01 ± 0.66 |
| 48 | 2.48 ± 0.71 | 2.55 ± 0.99 |

[1]Residual moisture before the treatment: 0.1 to 0.3 weight %
[2]Residual moisture before the treatment: 0.2 to 0.3 weight %

Further, pancreatin samples which were spiked with reoviruses (also termed "REO" in the following) were investigated. The residual moisture of these samples was 0.2 to 0.3 weight %. The influence on reoviruses of the heat treatment at 80° C. is shown for two series of experiments in Table 2:

TABLE 2

| Time [h] | Series No 1<br>Reduction Factors<br>[log₁₀] ± Standard Deviation | Series No 2<br>Reduction Factors<br>[log₁₀] ± Standard Deviation |
|---|---|---|
| 32 | 1.77 ± 0.37 | 1.72 ± 0.31 |

Further, control experiments were carried out under the same method conditions with control samples which differ from the samples according to the invention only in terms of the residual moisture. The control samples had a residual moisture between from 2.0 to 3.0 weight % (Table 3).

TABLE 3

| | Reduction Factor (log₁₀) | | |
|---|---|---|---|
| Virus | After 24 h | After 32 h | After 48 h |
| REO—80° C. Heating Step Residual Moistures <3% | 3.22 +/− 0.34 | 1.14 +/− 0.34 | 3.13 +/− 0.31 |
| | 4.13 +/− 0.89 | 1.05 +/− 0.31 | 3.22 +/− 0.34 |
| REO—80° C. Heating Step Residual moistures <0.5% | 1.59 +/− 0.37 | 1.77 +/− 0.30 | 0.87 +/− 0.35 |
| | 1.42 +/− 0.29 | 1.72 +/− 0.37 | 0.91 +/− 0.28 |
| PPV—80° C. Heating Step Residual Moistures <3% | 1.31 +/− 0.42 | 2.53 +/− 0.47 | 2.44 +/− 0.48 |
| | 2.81 +/− 0.96 | 2.36 +/− 0.30 | 2.81 +/− 0.96 |
| PPV—80° C. Heating Step Residual moistures <0.5% | 1.81 +/− 0.40 | 2.28 +/− 0.38 | 2.24 +/− 0.71 |
| | 2.00 +/− 0.47 | 2.01 +/− 0.66 | 2.55 +/− 0.99 |

*lower analysis number (no large volume plating)

The investigations into virus reduction by heating at very low residual moisture contents of the pancreatin (<0.5%) gave reduction factors which lay in the range of the investigations at higher residual moisture contents. It could therefore be shown that PPV is effectively inactivated even at low residual moistures and, at the same time, the enzyme activity is less severely reduced.

The inactivation of reovirus is, by contrast, more markedly dependent on the residual moisture of the dried pancreatin. Inactivations at residual moistures of 2.5% (<3%) gave reduction factors >3 (24 and 48 hours), while for the heat treatment at residual moistures of 0.2 to 0.3% (<0.5%) reduction factors in the region of 1.75 log stages (32 hours) were determined. Nonetheless, even at low residual moisture the influence of dry heat on the reduction of reovirus remains significant.

The results show that the method according to the invention guarantees a significant virus reduction.

Sample Production and Test Methods Used

Heat Treatment of PPV-Spiked Samples with a Residual Moisture of 0.5 Weight % or Less Untreated pancreatin samples were first spiked with viruses. Then, the spiked pancreatin samples were lyophilized in order to set the necessary residual moisture. The samples obtained then were finally subjected to a heat treatment.

Lyophilization Method 1.5 g of pancreatin raw material (ECSM Ch.: 0677 005-P, Nordmark Arzneimittel GmbH & Co. KG) were re-suspended with 3.2 ml PBS and agitated. The phials were then spiked with 0.3 ml of virus. The phials were provided with 0.3 ml of virus dilution medium for temperature control and to determine the residual moisture. The content of all phials was then agitated using a magnetic stirrer. The phials were placed in a freeze drier set to −30° C. in order to obtain a corresponding temperature of −25° C. overnight.

The lyophilization was carried out under a vacuum at 20° C. for 16 hours, whereupon an increase of the temperature to 50° C. for 24 hours followed. The phials were sealed under vacuum. Directly after the end of the lyophilization, a sample was titrated and, for this purpose, dissolved in 5 ml of PBS. A 1:2000 dilution was carried out on all samples (with virus dilution medium) in order to achieve complete dissolution.

Determining the Residual Moisture

The residual moistures of the samples before the heat treatment were determined using known methods.

Heat Treatment

The heat treatment was carried out in an oven set to 80° C.±1° C. As soon as the oven temperature reached 79° C., the samples were placed in the oven and left there for the predetermined periods of time. The temperature was monitored during the process.

The samples were removed for immediate titration at the determined points in time. The samples were titrated directly and for that purpose dissolved in 5 ml of PBS. A 1:2000 dilution was carried out for all samples (with virus dilution medium) in order to achieve complete dissolution. The samples were cooled on ice before the titration.

Assay Method (Indirect TCID$_{50}$ Assay)

PK-13 cells were inoculated into 96 well culture plates. In addition, two further 96 well plates were inoculated with regard to negative and positive controls. Eight wells were inoculated with each dilution of the sample (25 ml/well). After the incubation for 70 minutes±10 minutes at 36° C.±2° C., 175 ml of cell growth medium was added to the plates (the inoculant was not removed). The assay was carried out in accordance with SOP EPBT0062 and the plates were evaluated with respect to the TCID$_{50}$ endpoint as cytophatogenic effect developed in the positive controls. The TCID$_{50}$ endpoint was calculated in accordance with the Spearman-Kärber method as described in SOP EPBT0062.

The results are shown in the Tables 1, 2 and 3 and also in FIG. 6.

What is claimed is:

1. A pancreatin product of reduced microbial and viral contamination produced by a method comprising the steps of:
   (a) providing pancreatin in solid form with a residual moisture of 0.5 weight percent (weight %) or less based on the weight of pancreatin provided and
   (b) subjecting the pancreatin provided in step (a) to a heat treatment at a temperature of 84° C. or less obtaining heat treated pancreatin wherein
   the biological activity of the heat treated pancreatin obtained in step (b) corresponds to at least 50 percent (%) of the biological activity of the pancreatin provided in step (a); and the viral infectiousness of the heat treated pancreatin obtained in step (b) is reduced by a factor of more than 1 $\log_{10}$ in comparison with the viral infectiousness of the pancreatin provided in step (a).

2. The pancreatin product according to claim 1, characterized in that
the biological activity of the heat treated pancreatin corresponds to at least 50 percent (%) of the biological activity of the pancreatin;
the viral infectiousness of the heat treated pancreatin is reduced by a factor of more than 1 $\log_{10}$ in comparison with the viral infectiousness of the pancreatin; and
the germ contamination of the heat treated pancreatin is smaller than 500 KBE/g.

3. The pancreatin product according to claim 1, characterized in that the residual moisture of the pancreatin provided in step (a) is 0.1 to 0.3 weight %.

4. The pancreatin product according to claim 1, characterized in that the heat treatment in step (b) is carried out at 80° C.

5. The pancreatin product according to claim 1, characterized in that the pancreatin provided in step (a) has a residual moisture of 0.3 weight % and the heat treatment in step (b) is carried out at a temperature of 80° C. and below.

6. The pancreatin product according to claim 1, characterized in that the biological activity of the heat treated pancreatin obtained in step (b) corresponds to at least 90 percent (%) of the biological activity of the pancreatin provided in step (a).

7. The pancreatin product according to claim 1, characterized in that the contamination with toxic substances of the heat treated pancreatin obtained in step (b) is not higher than the contamination of the pancreatin provided in step (a).

8. The pancreatin product according to claim 1, characterized in that the germ contamination of the heat treated pancreatin obtained in step (b) is smaller than 500 KBE/g.

9. The pancreatin product according to claim 1, characterized in that the heat treated pancreatin in step (b) is subjected to the heat treatment for a time period of 48 hours or less.

10. The pancreatin product according to claim 1, characterized in that the heat treated pancreatin in step (b) is subjected to the heat treatment for 12 to 32 hours.

11. The pancreatin product according to claim 1, characterized in that the pancreatin is obtained from porcine pancreas.

12. A method for producing pancreatin with reduced viral and microbial contamination, comprising the steps of:
(a) providing pancreatin in solid form with a residual moisture of 0.5 weight percent (weight %) or less based on the pancreatin provided;
(b) subjecting the pancreatin filter cake provided in step (a) to a heat treatment at a temperature of 84° C. and below obtaining heat treated pancreatin;
wherein
the biological activity of the heat treated pancreatin obtained in step (b) corresponds to at least 50 percent (%) of the biological activity of the pancreatin provided in step (a); and
the viral infectiousness of the heat treated pancreatin obtained in step (b) has been reduced by a factor of more than 1 $\log_{10}$ in comparison with the viral infectiousness of the pancreatin provided in step (a).

13. The method according to claim 12, characterized in that the residual moisture of the pancreatin provided in step (a) is 0.1 to 0.3 weight %.

14. The method according to claim 12, characterized in that the heat treatment of the heat treated pancreatin in step (b) is carried out at 80° C.

15. The method according to claim 12, characterized in that the pancreatin provided in step (a) has a residual moisture of 0.3 weight % and the heat treatment in step (b) is carried out at a temperature of 80° C. and below.

16. The method according to claim 12, characterized in that the biological activity of the heat treated pancreatin obtained in step (b) corresponds to at least 90 percent (%) of the biological activity of the pancreatin provided in step (a).

17. The method according to claim 12, characterized in that the contamination with toxic substances of the heat treated pancreatin obtained in step (b) is not higher than the contamination of the pancreatin provided in step (a).

18. The method according to claim 12, characterized in that the germ contamination of the heat treated pancreatin obtained in step (b) is smaller than 500 KBE/g.

19. The method according to claim 12, characterized in that the heat treated pancreatin in step (b) is subjected to the heat treatment for a time period of 48 hours or less.

20. The method according to claim 12, characterized in that the heat treated pancreatin in step (b) is subjected to the heat treatment for 12 to 32 hours.

21. A pancreatin product produced by the following steps:
(a) providing pancreatin in solid form with a residual moisture of about 0.1 to 0.3 weight percent (weight %) or less based; and
(b) subjecting the pancreatin provided in step (a) to a heat treatment at a temperature of 80° C. or less, obtaining heat treated pancreatin having a biological activity corresponding to:
(1) a bacterial load of less than 500 KBE/g;
(2) reduced viral contamination by a factor greater than 1 $\log_{10}$ as compared to the viral contamination of the pancreatin; and
(3) biological activity of at least 90 percent (%) of the biological activity of pancreatin.

22. The pancreatin product of claim 21, wherein heat treatment of step (b) is for a duration of from about 1 hour to 48 hours.

23. The pancreatin product of claim 21, wherein heat treatment of step (b) is for a duration of from about 8 hours to 48 hours.

24. The pancreatin product of claim 21, wherein heat treatment of step (b) is for a duration of from about 32 hours to 48 hours.

25. The pancreatin product of claim 21, wherein the pancreatin is porcine pancreas.

26. A pancreatin product with reduced microbial and viral contamination produced by the following steps:
(a) reducing pancreatic glands by comminuting;
(b) subjection of the comminuted pancreatic glands to autolysis obtaining pancreatin;
(c) filtering the pancreatin to obtain a sieve filtrate;
(d) precipitation of enzymes contained in the sieve filtrate obtained by the filtration;
(e) filtration of the enzymes of step (d) to obtain pancreatin in solid form;

(f) grinding the pancreatin in solid form;
(g) drying the pancreatin in solid form by vacuum to a residual moisture of 0.5 percent weight (weight %) in relation to the provided vacuum-dried pancreatin in solid form; and
(h) subjecting the pancreatin in solid form to a heat treatment at a temperature of 84° C. or less, obtaining heat treated pancreatin.

27. The pancreatin product according to claim 26, characterized in that
the biological activity of the heat treated pancreatin corresponds to at least 50 percent (%) of the biological activity of the pancreatin;
the viral infectiousness of the heat treated pancreatin is reduced by a factor of more than 1 $\log_{10}$ in comparison with the viral infectiousness of the pancreatin; and
the germ contamination of the heat treated pancreatin is smaller than 500 KBE/g.

28. The pancreatin product according to claim 26, characterized in that the residual moisture of the pancreatin provided in step (g) is 0.1 to 0.3 weight %.

29. The pancreatin product according to claim 26, characterized in that the heat treatment in step (h) is carried out at 80° C.

30. The pancreatin according to claim 26, characterized in that the pancreatin provided in step (g) has a residual moisture of 0.3 weight % and the heat treatment in step (h) is carried out at a temperature of 80° C. and below.

31. The pancreatin product according to claim 26, characterized in that the biological activity of the heat treated pancreatin obtained in step (b) corresponds to at least 90 percent (%) of the biological activity of the pancreatin provided in step (a).

32. The pancreatin product according to claim 26, characterized in that the contamination with toxic substances of the heat treated pancreatin obtained in step (h) is not higher than the contamination of the pancreatin provided in step (g).

33. The pancreatin product of claim 26, wherein the pancreatic glands are porcine pancreas.

34. The pancreatin product of claim 26, wherein the subjection to autolysis of step (b) is by medium of one or more solvents from the group of water, acetone, isopropanol, or mixtures thereof such as aqueous isopropanol.

35. The pancreatin product of claim 26, wherein heat treatment of step (h) is for a duration of from about 1 hour to 48 hours.

36. The pancreatin product of claim 26, wherein heat treatment of step (h) is for a duration of from about 8 hours to 48 hours.

37. The pancreatin product of claim 26, wherein heat treatment of step (h) is for a duration of from about 32 hours to 48 hours.

38. The pancreatin product of claim 26, wherein the heat treated pancreatin obtained in step (h) consists essentially of a biological activity corresponding to
(1) a bacterial load of less than 500 KBE/g;
(2) reduced viral infectiousness by a factor greater than 1 $\log_{10}$ as compared to the viral contamination of the pancreatin; and
(3) biological activity of at least 90 percent (%) of the biological activity of pancreatin.

39. A pancreatin product with reduced microbial and viral contamination produced by the following steps:
(a) providing pancreatin glands with a residual moisture of about 0.5 weight percent (weight %) or less based on the weight of pancreatin provided;
(b) mincing the pancreatic glands;
(c) subjecting of the minced pancreatic glands to autolysis to obtain an intermediate product;
(d) filtering the intermediate product, obtaining a sieve filtrate with pancreatin having a microbial load of less than 500 KBE/g;
(e) precipitating the enzymes contained in the sieve filtrate to obtain a mixture;
(f) filtering of the mixture to obtain a pancreatin filter cake;
(g) grinding the pancreatin filter cake;
(h) drying the pancreatin filter cake grounds by vacuum to a residual moisture of between about 0.1 and about 0.3 percent weight (weight %) in relation to the provided vacuum-dried ground pancreatin filter cake;
(i) subjecting the vacuum dried untreated pancreatin to a heat treatment at a temperature of between about 70° C. and about 80° C. to obtain a heat treated pancreatin filter cake; and
(j) grinding the heat treated pancreatin filter cake to a pancreatin end product.

40. The pancreatin product according to claim 39, wherein the pancreatin glands are domestic pig pancreatin glands.

41. The pancreatin product according to claim 39, wherein the residual moisture of the pancreatin glands provided in step (a) is 0.1 to 0.3 weight percent (weight %).

42. The pancreatin product of claim 39, wherein the autolysis step (c) is by medium of one or more solvents from the group of water, acetone, isopropanol, or mixtures thereof such as aqueous isopropanol.

43. The pancreatin product according to claim 39, wherein the bacterial load of the sieve filtrate obtained in step (c) is less than 500 KBE/g.

44. The pancreatin product according to claim 39, wherein the heat treatment is carried out at 80° C.

45. The pancreatin product according to claim 39, wherein the residual moisture of the heat treated pancreatin filter cake is 0.3 weight percent (weight %).

46. The pancreatin product of claim 39, wherein the pancreatin end product has a bacterial load of less than about 500 KBE/g.

47. The pancreatin of claim 46, wherein the bacterial load of less than about 100 KBE/g.

48. The pancreatin product of claim 39, wherein the pancreatin end product has a reduced viral infectiousness by a factor greater than 1 $\log_{10}$ as compared to the viral contamination of the pancreatin.

49. The pancreatin product of claim 48, wherein the reduced viral infectiousness is by a factor greater than 3 $\log_{10}$ as compared to the viral contamination of the pancreatin.

50. The pancreatin product of claim 49, wherein the reduced viral infectiousness is by a factor greater than 4 $\log_{10}$ as compared to the viral contamination of the pancreatin.

* * * * *